(12) United States Patent
Fusch et al.

(10) Patent No.: US 9,492,603 B2
(45) Date of Patent: Nov. 15, 2016

(54) ARTIFICIAL PLACENTA

(75) Inventors: Christoph Fusch, Dundas (CA); Leslie Berry, Burlington (CA); Anthony Chan, Ancaster (CA); Niels Rochow, Hamilton (CA); Ponnambalam (Ravi) Selvaganapathy, Dundas (CA); John Brash, Ancaster (CA); Gerhard Fusch, Ancaster (CA)

(73) Assignee: McMaster University, Hamilton, Ontario (CA)

( * ) Notice: Subject to any disclaimer, the term of this patent is extended or adjusted under 35 U.S.C. 154(b) by 245 days.

(21) Appl. No.: 14/240,131

(22) PCT Filed: Aug. 23, 2012

(86) PCT No.: PCT/CA2012/000792
§ 371 (c)(1),
(2), (4) Date: May 26, 2014

(87) PCT Pub. No.: WO2013/026148
PCT Pub. Date: Feb. 28, 2013

(65) Prior Publication Data
US 2014/0255253 A1   Sep. 11, 2014

Related U.S. Application Data

(60) Provisional application No. 61/526,288, filed on Aug. 23, 2011.

(51) Int. Cl.
*A61M 1/16* (2006.01)

(52) U.S. Cl.
CPC ........ *A61M 1/1698* (2013.01); *A61M 2240/00* (2013.01)

(58) Field of Classification Search
CPC .................................................. A61M 1/1698
See application file for complete search history.

(56) References Cited

U.S. PATENT DOCUMENTS

| 4,154,792 A | 5/1979 | Miller et al. |
| 4,351,797 A | 9/1982 | Bellhouse et al. |

(Continued)

FOREIGN PATENT DOCUMENTS

CA    1046426 A    1/1979

OTHER PUBLICATIONS

El-Ferzli G T, Philips III J B, Bulger A, Ambalavanan N. (2009) A pumpless lung assist device reduces mechanical ventilation-induced lung injury in juvenile piglets. Pediatric Research 66(6): 671-6.

(Continued)

*Primary Examiner* — Philip R Wiest
*Assistant Examiner* — Benjamin Klein
(74) *Attorney, Agent, or Firm* — Gowling WLG (Canada) LLP

(57) ABSTRACT

An artificial placenta oxygenating device for use with an infant is provided. The device comprises a first layer comprising a gas permeable membrane; and a second layer comprising a vascular network that permits circulation of fluid therethrough, wherein a portion of the gas permeable membrane is attached to and covers the vascular network, wherein the vascular network comprises an inlet that permits fluid flow into the vascular network and an outlet that permits fluid to flow out of the vascular network and wherein the inlet and outlet are positioned so that fluid flows through the vascular network and in contact with the gas permeable membrane to permit gas exchange to occur. Assemblies comprising a plurality of single artificial placenta devices is also provided.

11 Claims, 17 Drawing Sheets

(56) References Cited

U.S. PATENT DOCUMENTS

| | | | |
|---|---|---|---|
| 4,411,872 A | 10/1983 | Bramson et al. | |
| 5,207,639 A | 5/1993 | Cooper | |
| 2011/0290113 A1* | 12/2011 | Borenstein .......... | A61M 1/1698 95/54 |

OTHER PUBLICATIONS

El-Ferzli GT, Philips III J B, Bulger A, Ambalavanan N. (2009) Evaluation of a pumpless lung assist device in hypoxia-induced pulmonary hypertension in juvenile piglets. Pediatric Research 66(6): 677-81.

Reoma, J. L. et al: "Development of an artificial placenta I: pumpless arterio-venous extracorporeal life support in neonatal sheep model", Journal of Pediatric Surgery, W.B. Saunders Company US, vol. 44, No. 1 Jan. 20, 2009, pp. 53-59.

Hung, T K et al.: "Transport and flow phenomena in a microchannel membrane oxygenator.", Annals of Biomedical Engineering Dec. 1977, vol. 5, No. 4, Dec. 1977, the whole document, p. 344, line 19-line 42: figure 1.

Griffith B.P. et al.: Arteriovenous ECMO for neonatal respiratory support. A study in perigestational lambs:, Journal of Thoracic and Cardiovascular Surgery, Mosby-year Book, Inc., St. Louis, MO, US, vol. 77, No. 4, Apr. 1, 1979, pp. 595-601, whole document, pp. 596; figure 2.

Raymond, H.W. Lam et al.: "Culturing Aerobic and Anaerobic Bacteria and Mammalian Cells with a Microfluidic Differential Oxygenator", Analytical Chemistry, vol, 81, No. 14, Jul. 15, 2009, pp. 5918-5924, the whole document.

Niels Rochow et al.: "Integrated microfluidic oxygenator bundles for blood gas exchange in premature infants", Micro Electro Mechanical Systems (MEM), 2012 IEEE 25th International Conference on, IEEE, Jan. 29, 2012, pp. 957-960.

Jutta Arens et al.: "NeonatOx: A Pumpless Extracorporeal Lung Support for Premature Neonates", Artifical Organs, vol. 35, No. 11, Oct. 14, 2011, pp. 997-1001.

Rochow Niels et al: "Artifical placenta-lung assist devices for term and premature newborns with respiratory failure", The International Journal of Artificial Organs Jun. 25, 2013, vol. 36, No. 6, pp. 377-391.

* cited by examiner

A)

B)

ARTIFICIAL PLACENTA

FIELD OF THE INVENTION

The present invention relates to treatment of respiratory failure in infants, and in particular, to an artificial placenta device for such treatment.

BACKGROUND OF THE INVENTION

Respiratory failure is the major cause of mortality and long-term morbidity of very low birth weight infants. Currently, mechanical ventilation is the method of choice to treat newborns with severe respiratory failure but the risk of lung damage using such methods is high. Associated impairments may result in a life-long dependency on mechanical ventilation.

Preterm infants (22 to 36 weeks) are born during the canalicular stage of development. At this age the lungs have not fully developed and capacity for gas exchange is low. The preterm lung has a lack of surfactant causing the alveoli to collapse. Without surfactant, alveolar spaces become wet as surface tension forces increase and draw more fluid from capillaries into the alveolar airspace. As this fluid accumulates, a hyaline membrane lining accumulates consisting of fibrin, red blood cells and other cellular debris. This leads to the hyaline membrane disease or infant respiratory distress syndrome (IRDS). Pneumonia can also lead to fluid accumulation and inflammation which results in increased respiratory rate, low oxygen saturation and nausea. The hyaline membrane disease can be prevented by giving mothers who are about to deliver prematurely a group of glucocorticoid hormones such as cortisol. This will accelerate the production of surfactant. For extremely premature birth, glucorticoids are given without testing. For fetuses older than 30 weeks, their fetal lung maturity is tested by inserting a needle through the mother's uterus and obtaining the surfactant concentration in the amniotic fluid. This is used to evaluate and correlate the amount of hormone needed to be delivered.

If RDS cannot be prevented, various ways to ventilate the baby are available to allow time for the lungs to heal. Mechanical ventilation is the prime method of ventilating babies with RDS. In mechanical ventilation, an endotracheal tube is inserted into the mouth or nose and advanced to the trachea. In mechanical ventilation, breathing is provided based on a set time. In HFOV (high frequency oscillatory ventilation), high respiratory rates (>60 breaths/min) are employed in small tidal volumes. In high frequency jet ventilation (HFJV), brief "jets" of gas are exerted out of the endotracheal tube into the airway. Since the exhalation is passive, induced lung injury is reduced. Another method of ventilation is iNO (inhaled nitrogen oxide). Inability to breath properly leads to pulmonary hypertension. Nitric oxide helps regulate muscle tone in arteries and lungs. However, this can lead to haemorrhage and is toxic if used in high amounts. Although ventilation is a useful practice, it does come with its risks. Absolute pressures used to ventilate non-compliant lungs can cause lungs to collapse and become physically damaged. The pressure differences that are created between the air space and the surrounding tissue lead to barotrauma. Also, lung injury from ventilators, or infection from ventilator tubes, can lead to chronic lung disease.

Current commercial neonatal oxygenators with a hollow fiber design have priming volumes as low as 40-43 mL (Schwenkglenks et al., 2011; Tinius, Dragomer, Klutka, VanBebber, & Cerney, 2003). This is unsuitable for very low birth weight infants with a circulating blood volume of 60-100 mL/kg body weight (Nagano et al., 2005). Infants that are 500-750 g, especially with a total blood volume of 30-71 mL, would require a much lower priming volume.

Various oxygenator designs have been applied in past artificial lung experiments. Some of the earliest studies commonly used rotating-disc oxygenators for perfusion (Alexander, Britton, & Nixon, 1968; J. C. Callaghan, Angeles, Boracchia, Fisk, & Hallgren, 1963; John C Callaghan, Maynes, & HUG, 1965; Lawn & McCance, 1962). This variant of the film oxygenator served dual purposes: to facilitate blood flow through the device and to allow for gas exchange in the blood. In the 1970 s, membrane lung devices became more widely used due to its effective gas exchange properties. Zapol et al (Zapol, Kolobow, Pierce JEVUREK, & Bowman, 1969), Bui et al (Bui et al., 1992), Awad et al (Awad et al., 1995) used coiled membrane oxygenators with priming volumes of 60-70 mL and gas exchange areas between 0.4-0.8 $m^2$. Several microporous hollow fiber oxygenators with priming volumes between 90-100 mL and gas exchange areas of 0.3-0.5 $m^2$ were seen in the literature (Awad et al., 1995; Fujimori et al., 2001; Pak et al., 2002; Reoma et al., 2009), although non-microporous hollow fiber devices became more common within the last decade of artificial placenta study (Fujimori et al., 2001; Kuwabara et al., 1989; M Sakata, K Hisano, M Okada, & M Yasufuku, 1998; Unno et al., 1993; Masao Yasufuku, Katsuya Hisano, Masahiro Sakata, & Masayoshi Okada, 1998). Only one study among the literature used a microfluidic device in its experiments. Griffith et al (Griffith, Borovetz, Hardesty, Hung, & Bahnson, 1979) designed a microchannel oxygenator with high gas exchange properties and a priming volume of 80 mL/unit for perfusion of neonatal lambs. Thus, the filling volumes of commercial oxygenators used in animal models ranged from 60 mL to 200 mL. Due to such a large priming volume, commercial oxygenators may not be well suited for perfusion in human neonates and it would be desirable to develop an oxygenator with a lower filling volume.

Another method for dealing with respiratory failure in extremely rare cases is extracorporeal membrane oxygenation (ECMO). ECMO provides cardiac and respiratory support to patients with damaged lungs and heart. Because ECMO is a highly invasive procedure where high volumes of blood need to be pumped from a blood vessel, passed through an oxygenator and then returned to the body, it requires monitoring of many mechanical and physiological variables. Babies less than 4.5 pounds have very small vessels and high resistance. This prevents adequate flow and is not the best option for preterm infants. Also, the mechanical pump of the ECMO circuit can cause shear stress injury to blood components and lead to complications with blood clotting. Failure of the oxygenator, pump failure, tubing rupture and cannula problems, can lead to intracranial bleeding, bleeding from the surgical site, seizures and infection.

The artificial heparin-coated lung was a breakthrough in oxygenator technology. The effectiveness of a hollow fiber silicone membrane oxygenator for ECMO use was tested. This newly improved model comprised increased fiber length and surface area, increased gas transfer rate, decreased density and pressure. Heparin diluted with saline was continuously administered to all compartments of the ECMO system to prevent clotting. However, this technology only partially replaces lung functions and would not provide 100% of total body gas exchange.

In view of the risks associated with ECMO and other ventilation procedures for preterm babies, there is a need for alternate methods of treatment.

SUMMARY OF THE INVENTION

An artificial placenta oxygenation device has now been developed which is particularly useful in neonates. The artificial placenta is a biocompatible, pumpless oxygenation device having a filling volume that renders it suitable for use with neonates. The device is adapted for connection to umbilical vessels, exhibits minimal damage to blood cells and may be treated to prevent coagulation.

Thus, in one aspect of the invention, an artificial placenta oxygenating device for use with an infant is provided comprising: a first layer comprising a gas permeable membrane and a second layer comprising a vascular network that permits circulation of fluid therethrough, wherein a portion of the gas permeable membrane is attached to and covers the vascular network, wherein the vascular network comprises an inlet that permits fluid flow into the vascular network and an outlet that permits fluid to flow out of the vascular network and wherein the inlet and outlet are positioned so that fluid flows through the vascular network and in contact with the gas permeable membrane to permit gas exchange to occur.

In another aspect, an oxygenating assembly is provided comprising a plurality of artificial placenta devices, wherein the assembly comprises a main inlet which is connected via an inlet channel to the inlets of each of the placenta devices, and a main outlet which is connected via an outlet channel to the outlets of each of the placenta devices.

This and other aspects of the invention will become apparent from the following description in which reference is made to the appended drawings.

DETAILED DESCRIPTION OF THE INVENTION

Figure 1A:
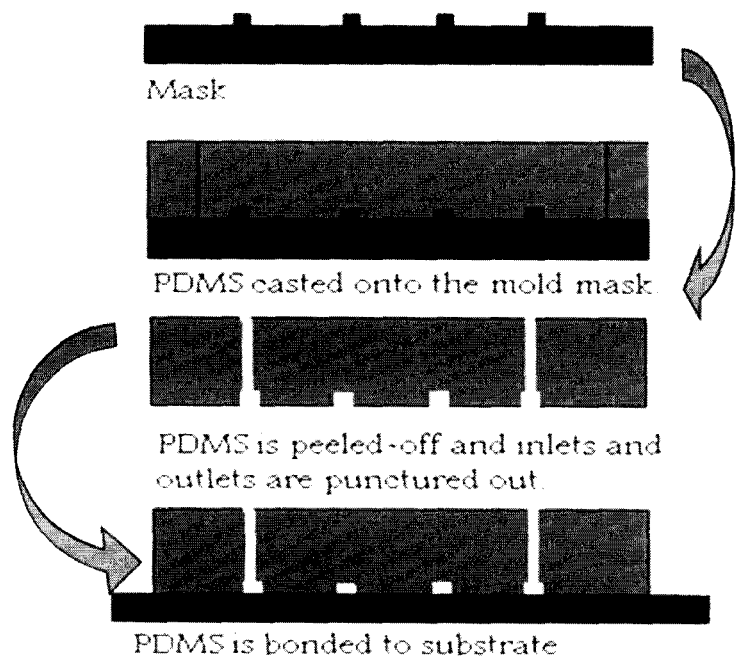
FIG. 1A shows the manufacturing process for an artificial placenta device according to the invention.
Figure 1B:
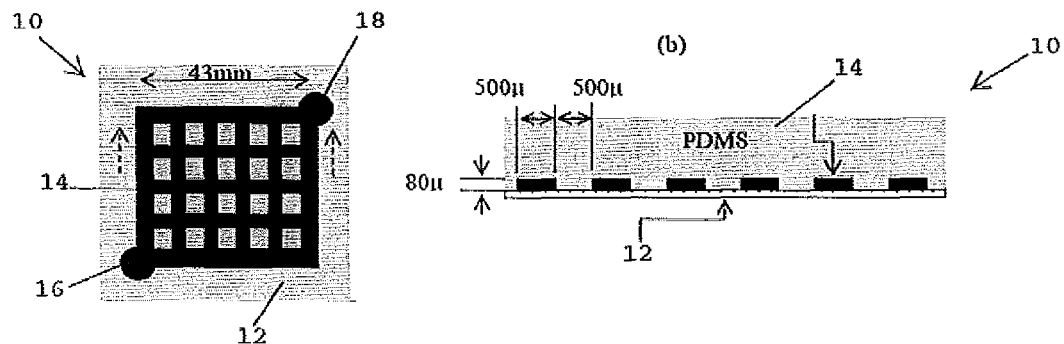
FIG. 1B illustrates a top view (a) and a sideview (b) of an artificial placenta device.

An artificial placenta oxygenating device for use with an infant is provided comprising: a first layer comprising a gas permeable membrane and a second layer comprising a vascular network that permits circulation of fluid therethrough, wherein a portion of the gas permeable membrane is attached to and covers the vascular network, wherein the vascular network comprises an inlet that permits fluid flow into the vascular network and an outlet that permits fluid to flow out of the vascular network and wherein the inlet and outlet are positioned so that fluid flows through the vascular network and in contact with the gas permeable membrane to permit gas exchange to occur.

The gas permeable membrane of the first layer of the device may be made out of any suitable natural or synthetic gas permeable polymeric material, including but not limited to, silicone-based organic polymers which are inert and non-toxic such polydimethylsiloxane (PDMS), polycarbonates, and other materials that exhibit sufficient permeability for oxygen, e.g. at least about 200 barrer, and carbon dioxide, e.g. at least about 500 barrer. The permeability of PDMS for oxygen is: 400-800 barrer, and for carbon dioxide is 2500-3800 barrer. Suitable membranes may have a thickness in the range of about 5-7 µm, preferably 6 µm, a pore size in the range of about 0.01-0.5 µm, preferably 0.05-0.1 µm, and a pore density in the range of about $1 \times 10^8$-$1 \times 10^9$ pores/cm$^2$, and preferably about $4 \times 10^8$-$6 \times 10^8$ pores/cm$^2$.

At least a portion of the gas permeable membrane is attached or fused to the vascular network such that one side of the membrane is exposed to the atmosphere (ambient air) and the other side is in contact with fluid (e.g. blood) within the vascular network to permit gas exchange within the fluid to occur, e.g. absorption of oxygen and removal of carbon dioxide. The vascular network includes an inlet that permits flow of fluid into the network, and an outlet that permits flow of fluid out of the network. The membrane and vascular network are fused using techniques known in the art.

The vascular network of the device is designed to permit fluid circulation therethrough and exhibits a surface-to-volume ratio of fluid (e.g. blood) which achieves sufficient gas exchange and is appropriate to maintain membrane integrity and minimize the pressure resistance and shear stress on the blood, for example, a surface-to-volume ratio of blood in the range of up to about 130 cm$^{-1}$, and preferably in the range of about 100 to 130 cm$^{-1}$, for example 125 cm$^{-1}$. It is also desirable to maximize gas exchange capacity by maximizing membrane density, i.e. the ratio of the membrane connected to the vascular network versus the total membrane area. A preferred membrane density is at least about 50%, preferably at least about 60%, and more preferably, at least about 70% or greater, e.g. between 70-90%. The vascular network is also designed to exhibit low pressure resistance, for example, lower than 20 mmHg, e.g. lower than 10 mmHg, and a shear stress throughout of the network that is below the blood coagulation threshold (10 Pa). The vascular network may be made of any material suitable for the manufacture of such a vascular network, including but not limited to, silicone-based organic polymers which are inert and non-toxic such polydimethylsiloxane (PDMS), polycarbonates and polyurethane. The vascular network may be made using techniques established in the art, for example, using the soft lithography process.

The inlet and outlet are conveniently adapted for connection to arteries and veins, respectively, and in the case of a newborn, to umbilical vessels of the newborn, i.e. umbilical artery and umbilical vein. Umbilical access may be achieved using commercially available umbilical catheters. The catheter for umbilical vascular access must be selected such that its resistance will not adversely affect the function of the placenta device, for example, a larger catheter with a size in the range of about 8-12 Fr, preferably about 10 Fr. Expandable catheters may also be utilized to provide greater flexibility and range of use.

The filling volume a single placenta device will vary with its configuration The device is designed to be applicable for newborn infants with weight range from about 400-4000 g. A single device is designed to accommodate about 100 grams of body weight, and thus, a filling volume in the range of about 0.2 to 0.6 mL, and preferably less than 0.3 mL. As will be described below, this filling volume may be increased by using multiple placenta devices in an assembly to achieve larger filling volumes, e.g. 1 mL-3 mL (500 g) to 8 mL-24 mL (4,000 g).

Figure 1C:
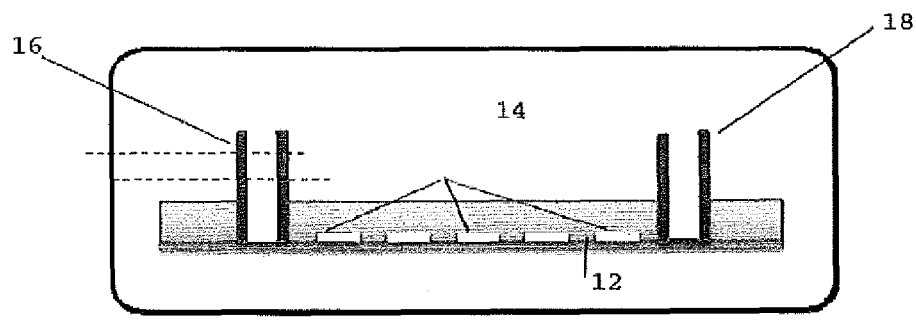
FIG. 1C illustrates the fabricated single unit membrane oxygenator with fluidic interconnection.

A schematic of the an embodiment of the present artificial placenta device 10 is provided in FIG. 1c. As shown, the device 10 comprises a membrane 12 fused to a vascular network 14. An inlet 16 feeds fluid into the vascular network 14 and may be connected to a catheter, such as an umbilical catheter, which is in turn connected to the umbilical artery. Blood to be oxygenated flows from the artery into the catheter and enters the device via inlet 16. The blood is then oxygenated as it passes through the vascular network 14 through gas permeable membrane 12 which is exposed to ambient air. An outlet 18 permits fluid, e.g. oxygenated blood, to exit from the vascular network 14 of the device into a catheter which feeds into the umbilical vein.

Blood contacting surfaces of the device, such as the membrane and vascular network surfaces, inlet/outlet internal surfaces, internal catheter surfaces and flow measurement and control devices, may be coated with molecules that inhibit immunological and coagulation responses. Examples of suitable anti-coagulant coatings include, but are not limited to, polyethylene oxide (PEO), mixed endothelial cells, silicone, and hydrophilic polymers, heparin anticoagulants such as heparin and heparin derivatives having the active pentasaccharide sequence and the covalent antithrombin-heparin (ATH) complex as described in U.S. Pat. No. 8,138,308, the contents of which are incorporated herein by reference. Heparin molecules including the active pentasaccharide sequence are covalently bound to antithrombin which is permanently activated by the covalently bound heparin. Covalent linkage of the active heparin to antithrombin in the ATH complex results in secure binding of heparin to surfaces and properly orients the heparin chain away from the surface to result in effective inhibition of blood coagulation.

To provide a greater range of use, the artificial placenta oxygenating device may be combined with one or more additional placenta devices in an assembly. Such an assembly advantageously provides the ability to treat newborns of a range of weights. For example, since a single device is appropriate per 100 g of body weight, an assembly comprising 4 placenta devices is suitable to treat a 400 g patient, while an assembly comprising 20 placenta devices is suitable to treat a 2 kg patient. The placenta devices may be combined in series or in parallel depending on the desired pressure-flow rate and shear stress characteristics. An assembly of placenta devices, thus, provides a unit with an increased filling volume and increased gas exchange capacity. Table 1 provides the pressure-flow characteristics of various placenta device assemblies in series and in parallel combinations.

Figure 10A:
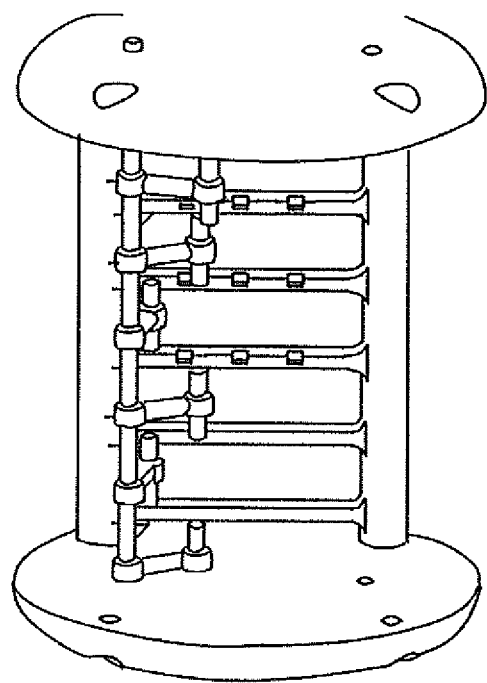
FIG. 10 shows a tube system for parallel combination of single placenta devices (A) and a system with connected placenta devices 10(B)
Figure 10B:
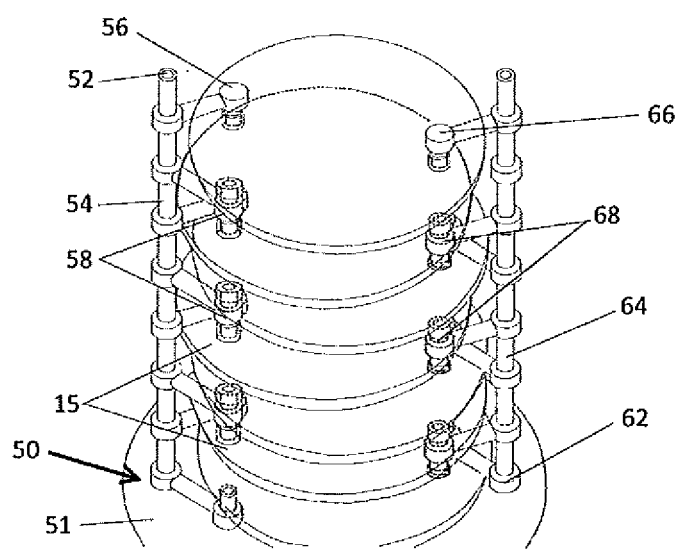
Figure 11A:
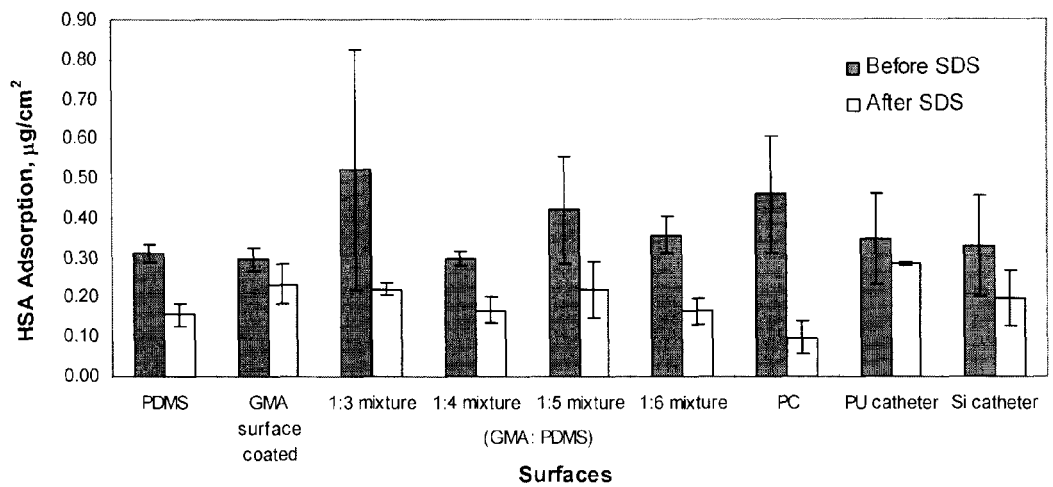
FIG. 11A shows an uptake of human serum albumin from PBS before and after elution with SDS. Untreated PDMS, modified PDMS surfaces (varying GMA: PDMS mixture ratios), polycarbonate (PC), a polyurethane (PU) catheter and a silicone (Si) catheter are compared.
Figure 11B:
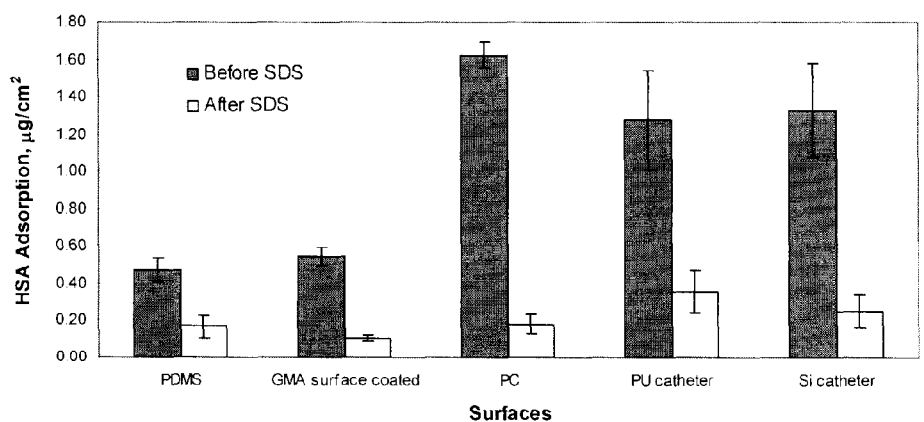
FIG. 11B shows an uptake of human serum albumin from PBS before and after elution with SDS. Untreated PDMS, modified PDMS surfaces with GMA coating, polycarbonate (PC), a polyurethane (PU) catheter and a silicone (Si) catheter are compared. Data are means±SD, n=4.
Figure 12:
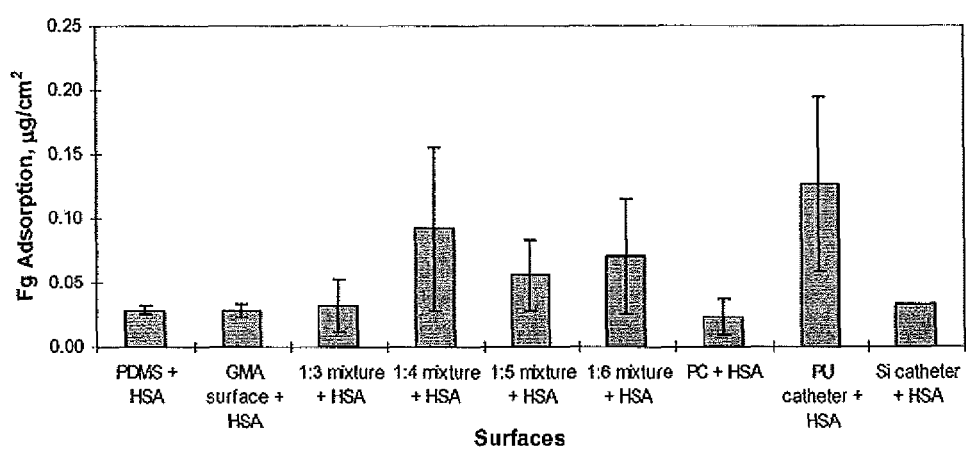
FIG. 12 shows the fibrinogen adsorption from plasma to albumin pre-adsorbed surfaces. Untreated PDMS, modified PDMS surfaces (varying GMA: PDMS mixture ratios), polycarbonate (PC), a polyurethane (PU) catheter and a silicone (Si) catheter are compared. Data are means±SD, n=3.
Figure 15:
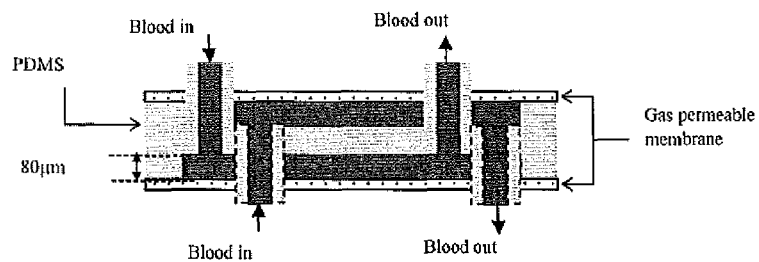
FIG. 15 depicts a back-to-back arrangement of a pair of placenta devices.

In one embodiment, an assembly of artificial placenta devices is provided in which there is a parallel connection of a plurality of placenta devices. In this assembly, pairs of placenta devices are connected back to back, e.g. the vascular network of each device is attached and the gas permeable membrane surfaces of each are exposed, to yield a back-to-back device with an inlet and outlet on both membrane-exposed faces, as illustrated in FIG. 15. A plurality of back-to-back devices 15 are then connected, in a spaced, adjacent arrangement, by a support device as illustrated in FIG. 10. The support device 50 comprises a main inlet 52 connected to an inlet channel 54 and a main outlet (not shown) connected to an outlet channel 64. Extending from the inlet channel 54 are channelettes 56, 58 adapted to attach to the inlets of each of the placenta devices. The channelettes 56 at the upper-most and lower-most end of the inlet channel 54 are adapted to connect to a single inlet on a placenta device, while channelettes 58 are adapted to connect to two inlets of adjacent back-to-back devices 15. The outlets of each back-to-back device are similarly connected to outlet channel 64 via outlet channelettes 66, 68. Blood to be oxygenated is flowed into the assembly through inlet 52 via a catheter, and is flowed through inlet channel 54 and into the placenta devices 15 via channelettes 56, 58. The blood flows through the vascular network of the devices 15 where gas exchange occurs and out of the device outlets, through outlet channelettes 66, 68, into the outlet channel 64 for exit out of the assembly through main outlet 62 and into a catheter for entry back into the patient.

Figure 18:
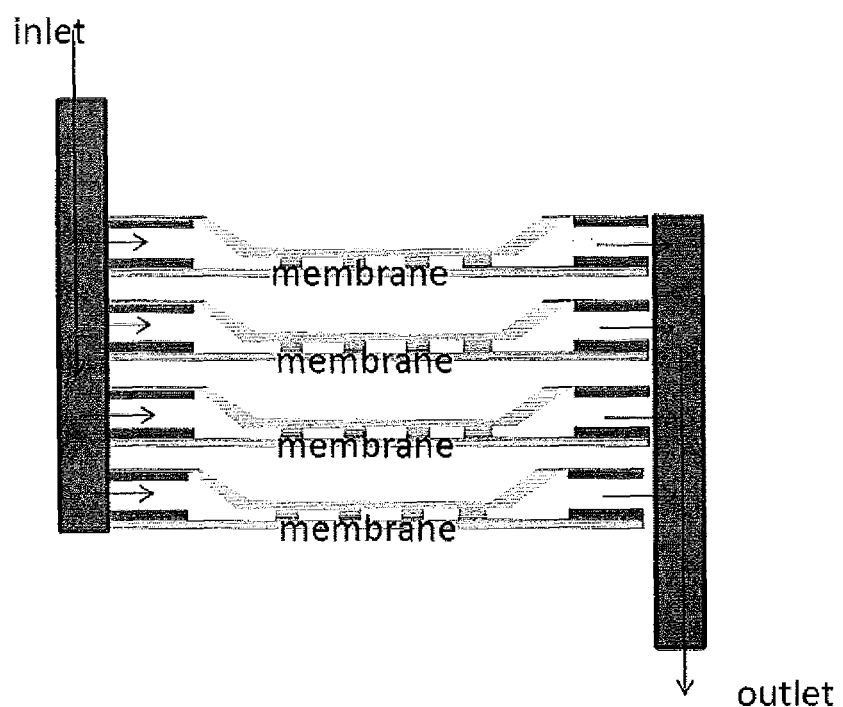
FIG. 18 illustrates an alternative embodiment.

In another embodiment, an assembly is provided in which a plurality of single placenta devices are connected as shown in FIG. 18. The placenta devices are positioned adjacent to one another and connected via a main inlet 60 and inlet channel 62, and a main outlet 70 and outlet channel 72. Connectors extending from the inlet channel 62 connect the channel 62 to the inlet of each placenta device. Likewise, connectors extending from the outlet channel 72 connect to the outlet of each placenta device. As in previous embodiments, blood from a patient is flowed via inlet 60 into the inlet channel 62 and disperses into the placenta devices where gas exchange occurs within the membrane-covered vascular network. Blood then flows out of the placenta devices via outlets into the outlet channel 72 and outlet 70 for delivery to the patient.

In order to control the blood flow, the device may be connected to a flow control unit. For example, blood flow through the device may be monitored by means such as a conventional extracorporeal clamp flow sensor device, and measured by appropriate means such as ultrasonic flow illumination. In addition, a blood pressure controller may be used to adjust the blood flow, e.g. hand wheel blood pressure controller.

The present artificial placenta device, and assemblies thereof, are designed for use in infants with a body weight of 500 to 4,000 g and exhibits an appropriate filling volume for this use. The device provides uniform distribution of blood flow, minimizes the shear force on the blood perfusate, and maximizes contact area between the perfusate and the permeable membrane to reach high levels of gas exchange The present device provides adequate oxygenation (e.g. at least about 10%, preferably at least about 20% and more preferably, at least about 30%), thereby providing a means to oxygenate neonatals with minimal risk.

Embodiments of the present invention are described by reference to the following specific example which is not to be construed as limiting.

Example 1

Preparation of an Artificial Placenta Device

A miniature artificial lung/placental device was developed for use in preterm babies. The device improves the efficiency of oxygenation in preterm babies since it is based on passive flow, is coated with heparin to prevent clotting and provides appropriate resistance with sufficient flow and small volume.

An approximately 3-inch microchannel mould was created to cast a PDMS (a silicone-based organic polymer) microchannel and then a membrane is attached to seal the channel. The specific process used to create a mold for the vascular microchannel network, prepare the vascular network and attach the membrane was as follows. The silicone substrate was cleaned as follows: rinsed with acetone for 15 sec., rinsed with methanol for 15 seconds and rinsed with de-ionized (DI) water for 5 min. The sample was dried using compressed nitrogen and dehydrated at 110° C. for 2 min.

The microchannel mould was prepared as follows. The silicone substrate was plasma oxidized at 50 W for 1 min., spun SU-8 100 for 30 sec at 3000 rpm and baked at 65° C. for 10 min and at 95° C. for 30 min. The substrate was then exposed using microchannel mould mask for 90 sec at 7.2 mJ/sec. The substrate was baked at 65° C. for 1 min and at 95° C. for 10 min, and then developed for 10 min in 1:3 SU-8 developer to distilled water solution. The substrate was rinsed with DI water for 5 min and hard-baked at 130° C. for 5 min.

The PDMS microchannel was then casted as follows and as shown in FIG. 1a. PDMS (15 ml) was mixed with 1.5 ml of curing agent. The mixture was then degasified in a dessicator for 5 min. The PDMS was poured over the microchannel mould and silicone tubes were positioned to form the inlet & outlet on top of the reservoir. The casted microchannel was baked at 65° C. for 1 hour and then the PDMS was carefully peeled off of the silicon substrate. The inlet & outlet were cleaned out with needles. The microchannel was treated with oxygen plasma for 1 min.

The PDMS thin membrane was fabricated as follows. 3M parafilm was cut into a 3" circle and placed on top of 3" wafer. A 3:1 PDMS/hexane mixture was poured onto the wafer, spun at 2000 rpm for 60 sec. and cured at 80° C. for 10 mins. The PDMS microchannel was placed on top of the PDMS mixture and cured at 90° C. for another 10 mins. The PDMS microchannel with membrane was then peeled from the parafilm. Blood contacting surfaces are then coated with anti-coagulant using methods known in the art.

Essentially, the microfluidic network was fabricated through the soft-lithography process. The molds were made by SU-8 photoresists as above resulting in 80 μm in height; however, the height may be greater or smaller. Silicone tubes that were used as the interconnections, were placed on top of the inlets and outlets, and subsequently the PDMS mixture (1:10) was cast on the mold. After the PDMS was cured, the microfluidic network with integrated interconnects was then peeled from the mold. Punch tools were used to clean residual PDMS inside the tubing.

Gas permeable PDMS and polycarbonate (PC) membranes were bonded to the microfluidic network via microcontact printing. The porous polycarbonate membranes were purchased from GE Water & Process Technologies and had a thickness of 6 μm. The membranes with 0.05 μm pore size had a pore density of $6 \times 10^8$ pores/cm$^2$, and membranes with 0.1 μm pore size had a pore density of $4 \times 10^8$ pores/cm$^2$. Subsequently, the bonding between microfluidic network and membranes was performed through the micro-contact printing using the PDMS mixture (1:10) as ink. The device is based on an orthogonally interconnected arrangement and high width: height ratio (width>height). In this embodiment, the height of each channel was about 0.1 mm and width was about 0.5-1.5 mm.

Example 2

In Vitro Testing of Artificial Placenta Device

Figure 2:
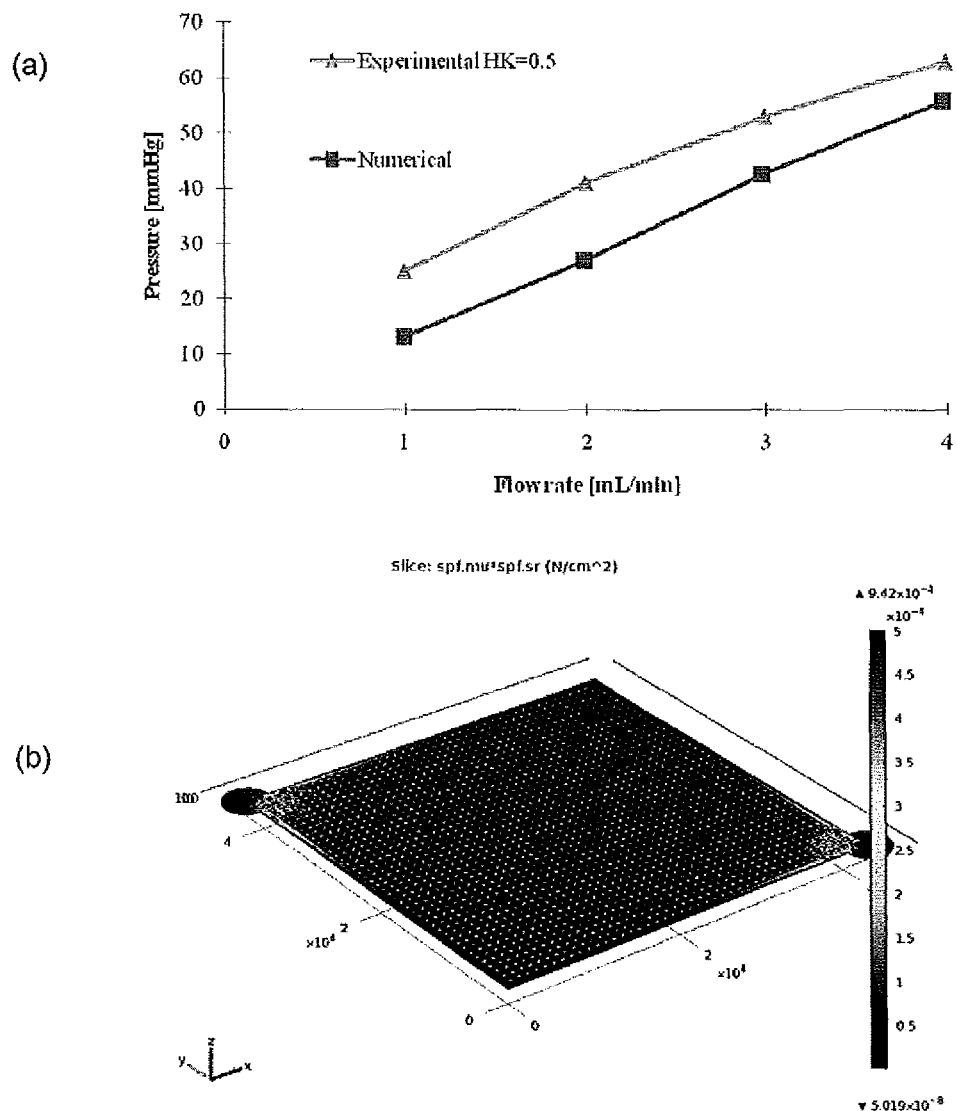
FIG. 2 graphically illustrates experimental and numerical pressure versus various flow rates (a) and a shear stress distribution at a blood flow of 1 mL/min (b) in an artificial placenta device.
Figure 3:
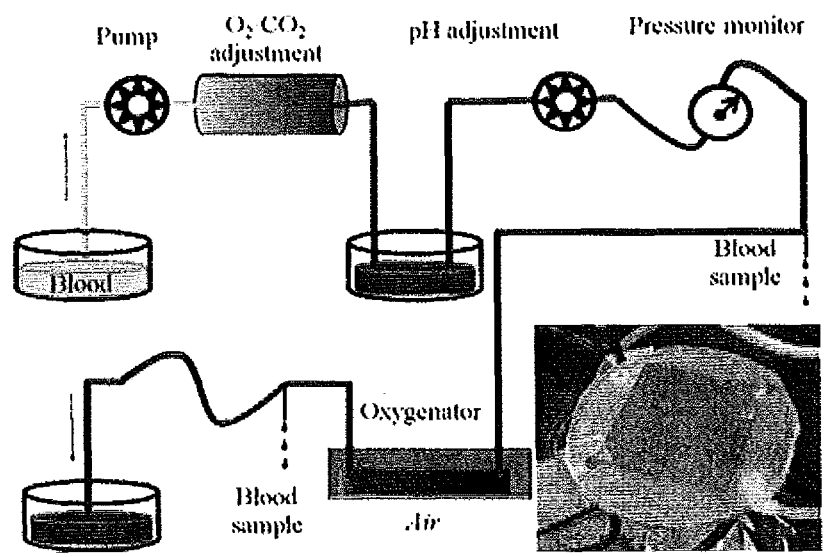
FIG. 3 is a flow diagram of in vitro gas exchange testing of the placenta device.
Figure 4:
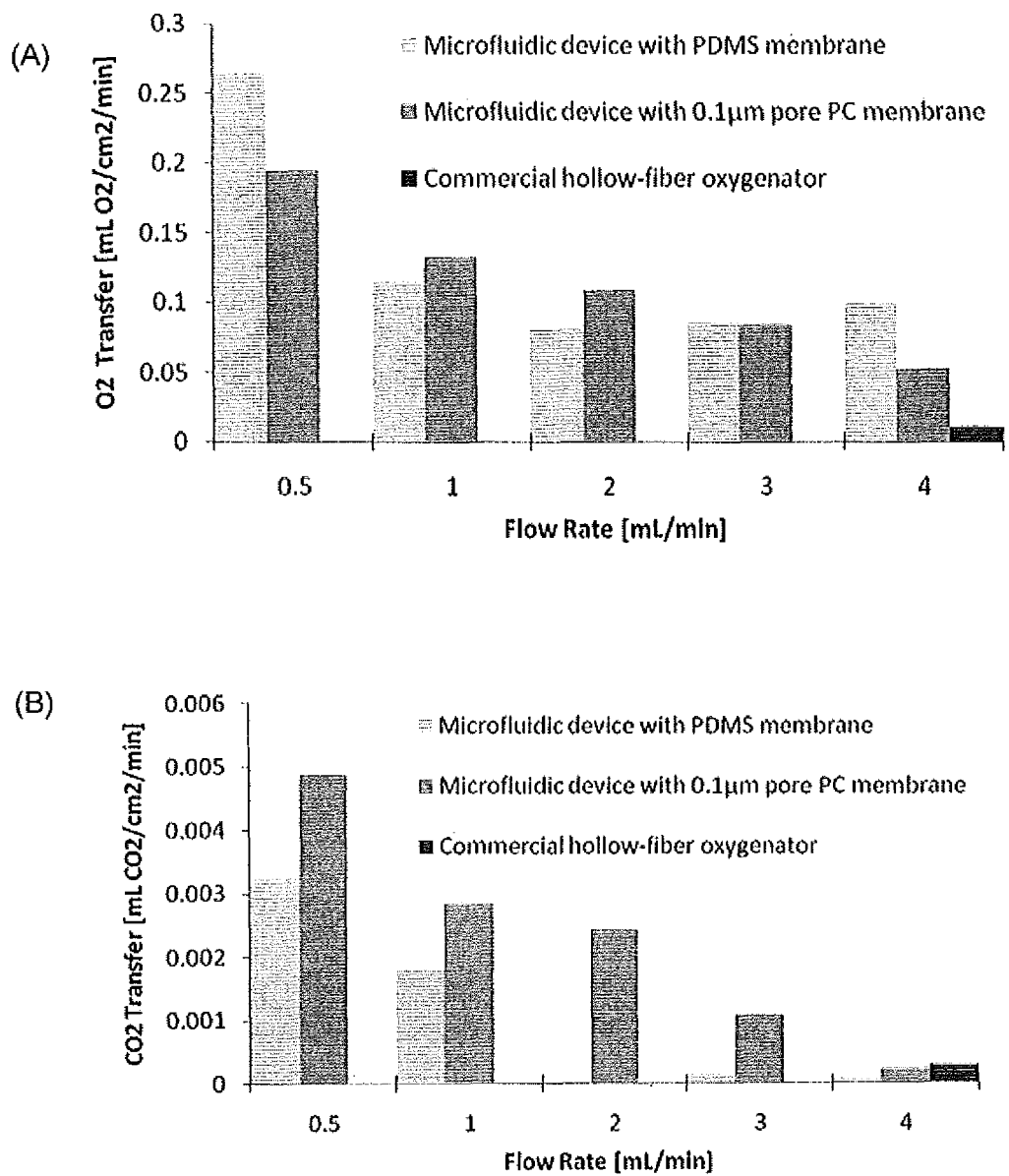
FIG. 4 graphically illustrates oxygen (A) and carbon dioxide (B) exchange characteristics of the placenta device with PDMS and PC membranes in comparison with a commercial hollow fiber oxygenator.
Figure 5:
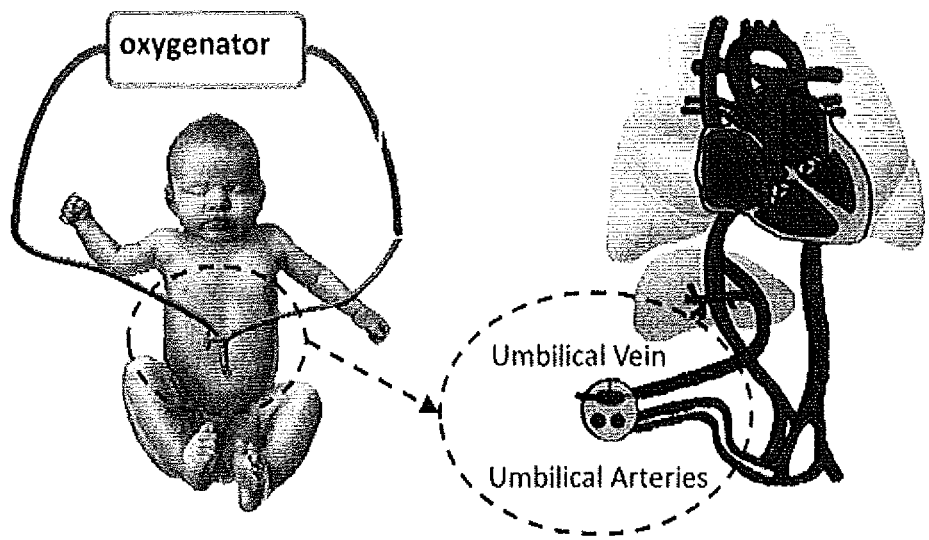
FIG. 5 is a schematic illustrating the connection of the device to the umbilical artery and vein.

For in-vitro testing of a placenta device as described in Example 1, human erythrocyte concentrates were adjusted with plasma for a hematocrit of 50%. pH was adjusted by adding NaHCO$_3$ and aerating with nitrogen. Heparin (3 units/mL) was added for anticoagulation. The blood was pumped through the gas exchange device at flow rates of 1~4 mL/min while the pressure was measured (FIG. 2a). Blood samples were collected before and after flowing through the membrane device according to the flow diagram of FIG. 3 to determine the gas exchange. The results show that the gas flux decreased with decrease in residence time (or increased flow rate) (FIG. 4). Both membranes were comparable in O$_2$ exchange. Both microfluidic devices with PDMS and PC membranes were compared to a commercial hollow-fiber based oxygenator OXR® and found to exhibit about a five-fold increase in $O_2$ flux.

Figure 7A:
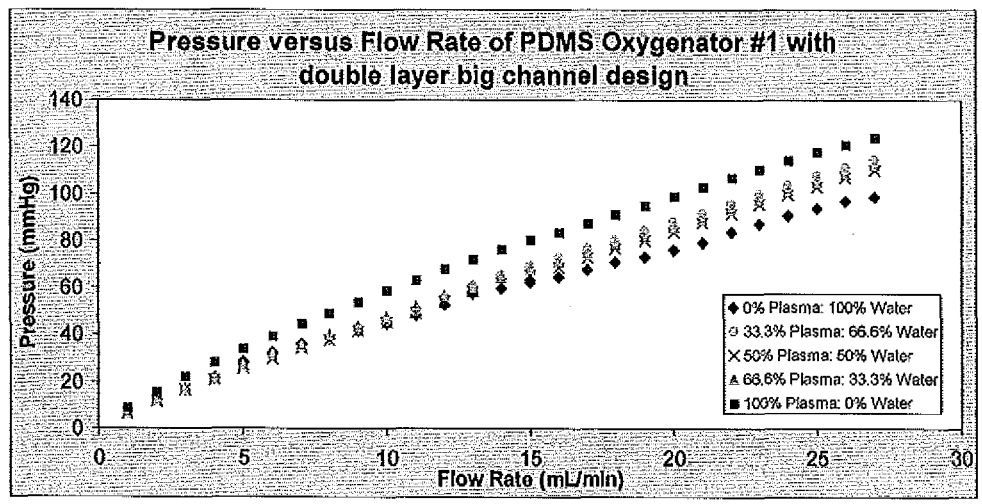
FIG. 7A illustrates resistance analysis in vitro of various plasma and water solutions in large channel placenta device.
Figure 7B:
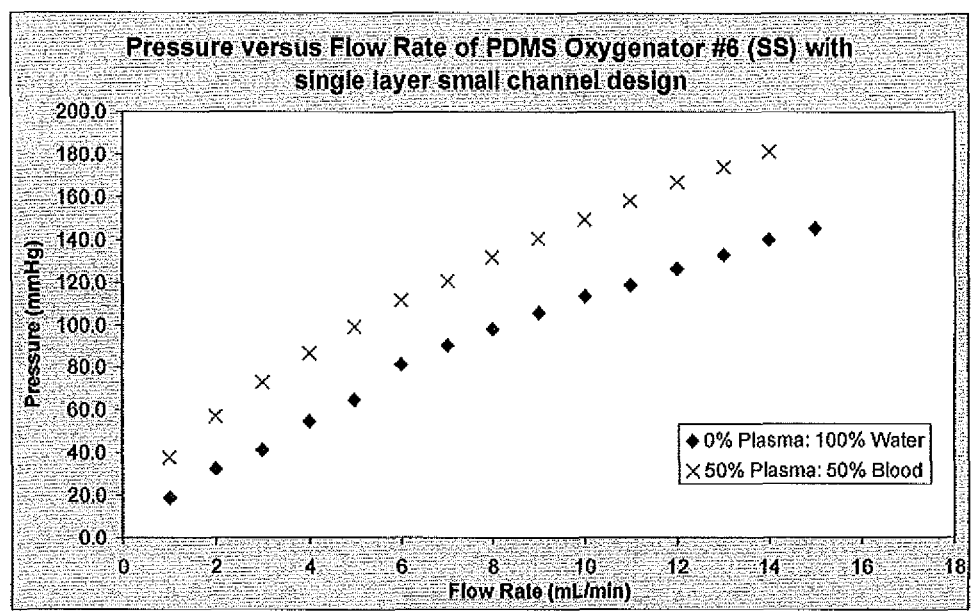
FIG. 7B illustrates resistance analysis in vitro of blood and water in a small channel placenta device.
Figure 7C:
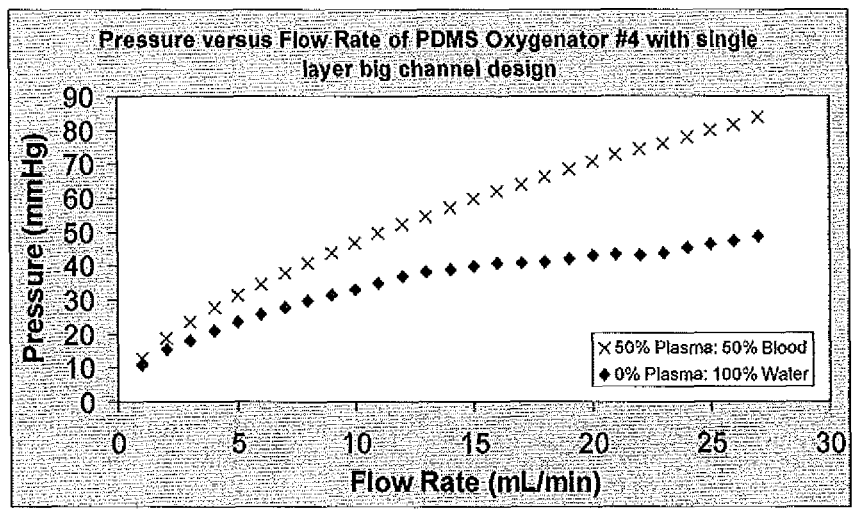
FIG. 7C illustrates resistance analysis in vitro of blood and water in a large channel placenta device.
Figure 8:
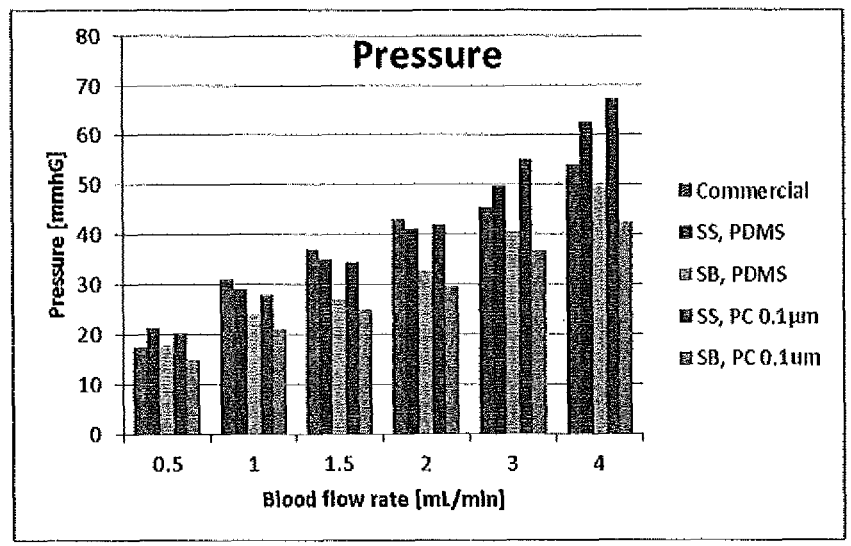
FIG. 8 illustrates resistance analysis in vitro of various placenta devices.

Fluids of various viscosities were flowed through the device to confirm that the device could be used with appropriate pressures and does not rupture. The corresponding flow rate to various pressures (above and below 60 mm Hg (40 mmHg to 60 mmHg) was obtained for each fluid. Following flow through devices at an optimal pressure that reflects the pressure exerted in vivo, the flow rate and gas exchange were measured pre-inlet and post-outlet using a blood gas-analyser. Pressure and flow setups as shown in FIG. 3 will run with blood of various viscosities (FIG. 7).

Based on current design, the pressure drop is 23 mmHg at a blood flow of 1 mL/min and increased to 59 mmHg at 4 mL/min as shown in FIG. 2a. A numerical model was used to verify the shear stress distribution to avoid pooling and clotting effects.

In this study, the effective membrane area and the total inner volume of the vascular network in a single device is 15.3 $cm^2$ and 0.122 $cm^3$, respectively, that result in a surface-to-volume ratio of 125 $cm^{-1}$.

Figure 9:
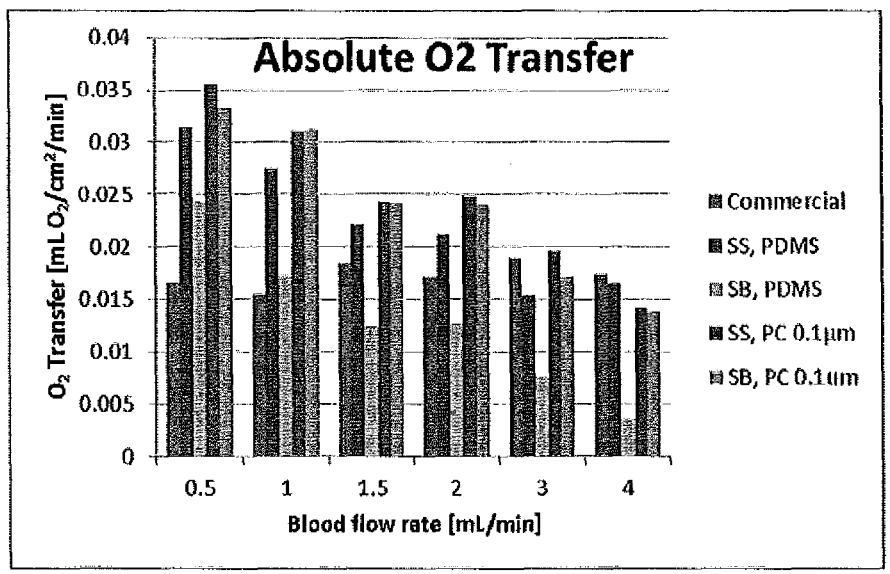
FIG. 9 graphically illustrates oxygen (A) and carbon dioxide (B) gas exchange characteristics of various placenta devices.
Figure 9:
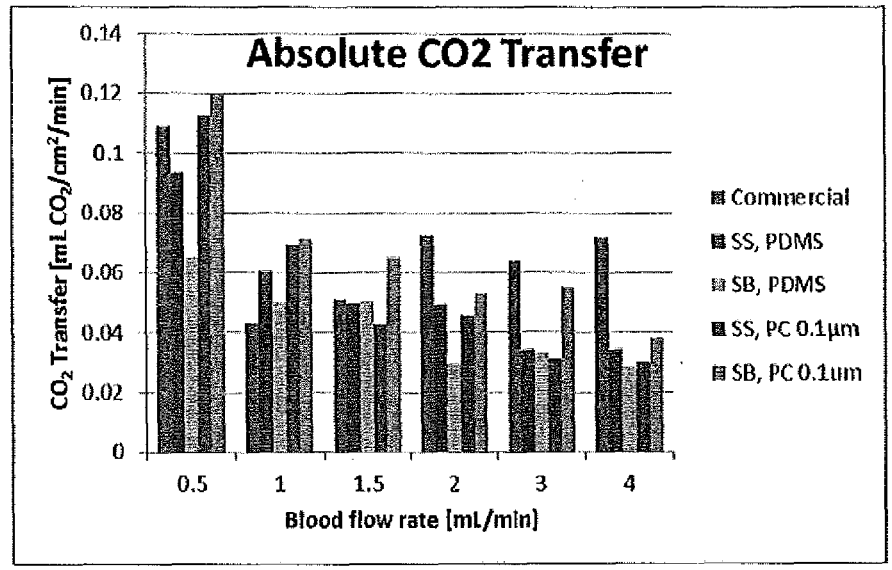

The results in FIG. 9 show that gas flux of both PDMS and PC membranes were comparable in $O_2$ (0.04 mL/min) and $CO_2$ (0.03 mL·$min^{-1}$) exchange. Microfluidic oxygenators with PC membranes outperformed the OXR® in $O_2$ flux while the average difference in $CO_2$ flux was 1.5 to 2 times higher. Surface-to-volume ratio in OXR® was 115 $cm^{-1}$.

Figure 6:
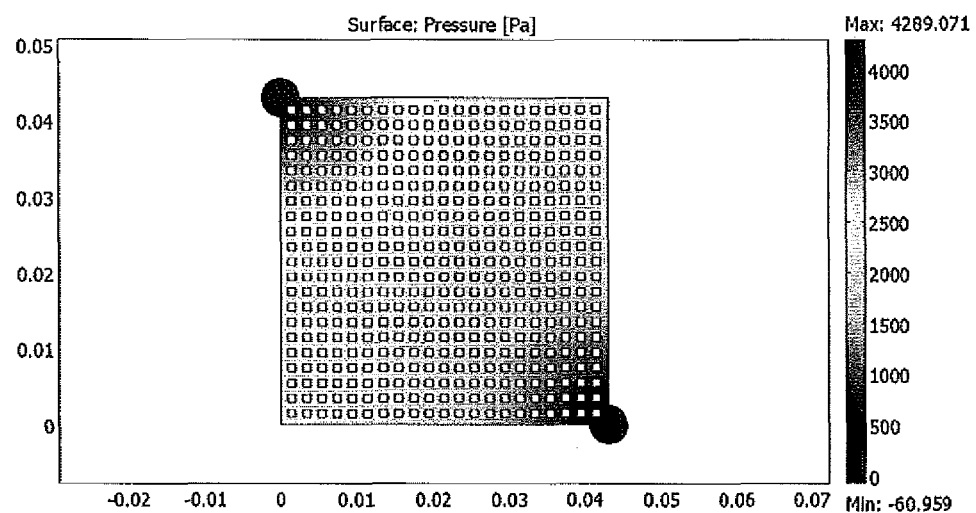
FIG. 6 illustrates a simulation of the pressure drop across the vascular network of the placenta device at a flow rate of multiple units.

Prototypes (in various combinations of small channel (500 µm width) and big channel (1,000 m width) combined with PDMS or polycarbonate membranes) of the present artificial oxygenating placenta devices were built. These were made with Poly Dimethyl Siloxane (PDMS). FIG. 6 shows theoretical calculations of pressure distribution in the device. These prototypes were intensively tested for their resistance characteristics using different perfusate media which also included blood. Subsequently, gas exchange rates while applying various physiological blood flow rates were analyzed.

The pressure flow curve obtained in FIG. 7 shows an exponential relationship between flow and pressure for plasma and water. The relative change in increase in pressure for plasma is indicative of its viscosity in relation to water. Plasma has a viscosity 1.5 times the water. It is assumed that the pressure-flow curve for blood will have an increased acceleration at least three times that of water since blood is 3× times viscous than water.

The small channel oxygenators performed better than big channel oxygenators (FIG. 7a-c) and the polycarbonate oxygenators performed better than the PDMS oxygenators at lower flow rates.

Example 3

Gas Exchange

Figure 16:
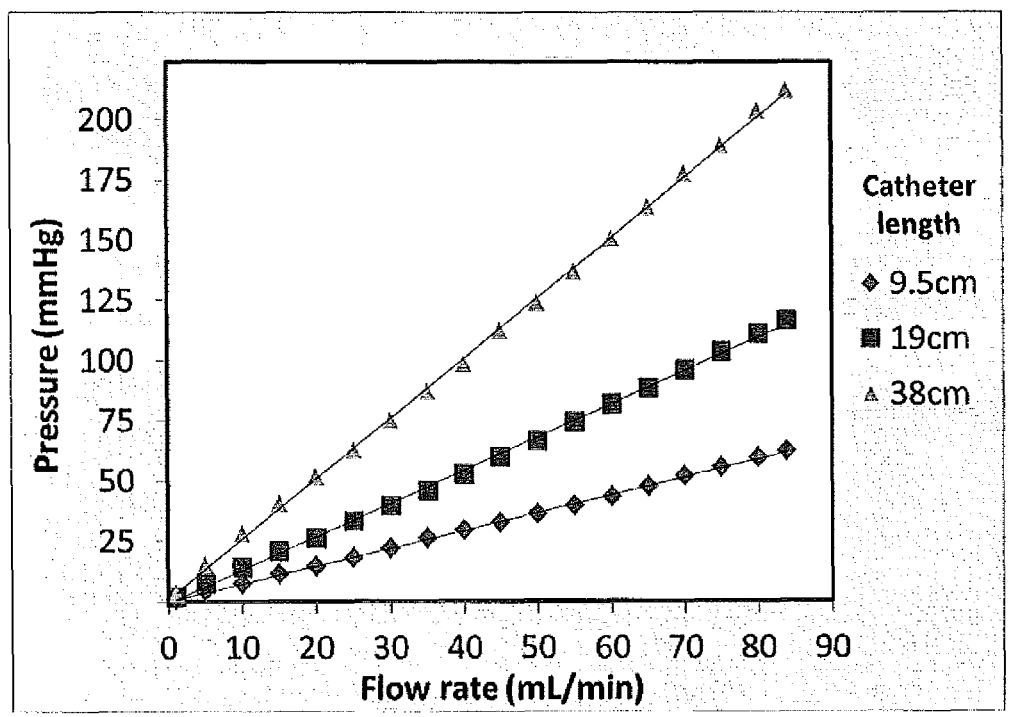
FIG. 16 graphically illustrates pressure flows of catheters of different lengths.
Figure 17:
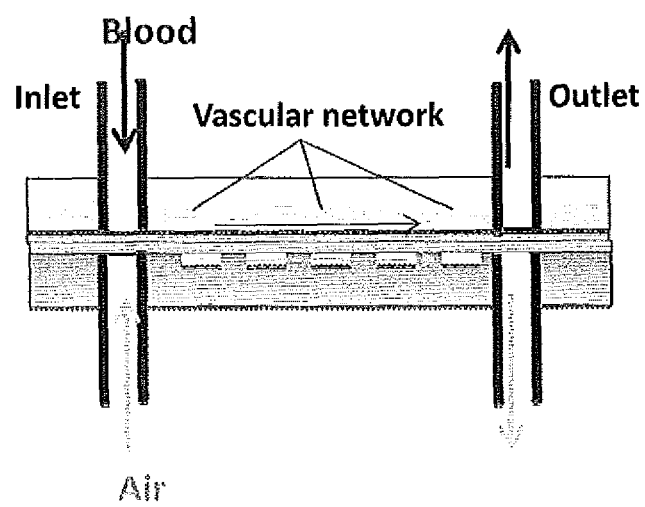
FIG. 17 illustrates an alternative embodiment.

To test gas-exchange, two channels were attached together such that the membranes involved in diffusion faced each other as shown in FIG. 17. The top channel was attached to a pump that pumped blood through the device. The bottom channel was attached to a gas supply of varying oxygen levels, e.g. 30% O2, 40% O2, 50% O2, no gas, room air and atmospheric conditions. The gas exchanger served to simulate blood in umbilical arteries before entering the placenta. As blood passed through the device, it passed along a concentrated supply of gases that diffused through and interacted with the blood. The resistance of the device was measured. If not enough blood passed through the device, adequate oxygenation did not occur. If a large volume of blood flowed through the device, sufficient blood did not circulate through the body, the carbon dioxide concentration decreased and oxygen concentration in the blood increased. A basic visualization is displayed in FIG. 16 modeling different catheter lengths and the resulting pressure.

Example 4

Placenta Device Assembly

A placenta device assembly was developed as a bundle of 14 devices stacked symmetrically in parallel. Two oxygenators were bound back to back as shown in FIG. 15 to reduce the dead volume in the connectors (<4 mL).

The assembly was constructed using components made from a 3D printer prototype. These hollow components with lower hydraulic resistance allowed a blood circulation as indicated in FIG. 6 and eliminated the pressure difference between each device. Furthermore, the distance between each device of the assembly and the main blood stream was kept the same to ensure uniform blood flow/pressure in each device was maintained.

This assembly of placenta devices exhibited satisfactory results in line with expectations based on the results for single placenta devices.

Example 5

Testing of Device Feasibility and Effectiveness with Piglets

To determine the device's ability to affect cardiac output, pulmonary arterial pressure, left atrial pressure, other hemodynamic variables and the extent to which the device aids extracorporeal membrane oxygenation, the device was tested in piglets.

Newborn piglets less than 1 day old with a body weight from 1.1-1.7 kg, strain Yorkshire, were used. Single placenta devices and device assemblies including 14 placenta devices, which were placed back-to-back in pairs and stacked parallel, were tested. The animal was anaesthetized. Continuous intravenous nutrition and systemic anticoagulation with heparin was supplied. The arterial catheter was placed in the carotid artery to monitor blood pressure. The piglet was incubated and placed under controlled ventilation.

After all monitoring devices had been connected to the animal, the placenta device (or assembly) was connected to the umbilical vessel using customized umbilical catheters (0.17×8 cm venous catheter, 0.12×11 cm arterial catheter). Humidified gas mixture 40% oxygen in nitrogen was delivered. A 3.5 Fr Argyle umbilical catheter was inserted into the left carotid artery and advanced to a 5 cm marking on the catheter. The catheter was secured, perfused with saline and used for blood sampling and continuous systemic blood pressure monitoring. The abdominal vein was cannulated with a 22 gauge angio catheter for maintenance of fluids and for the administration of maintenance sodium pentobarbital (16 mg/kg). An ISC probe was placed on the abdomen and temperature was monitored and maintained throughout the experiment at 39° C. The blood pressure monitor was connected to the calibrated Cobe pressure transducer.

Figure 13:
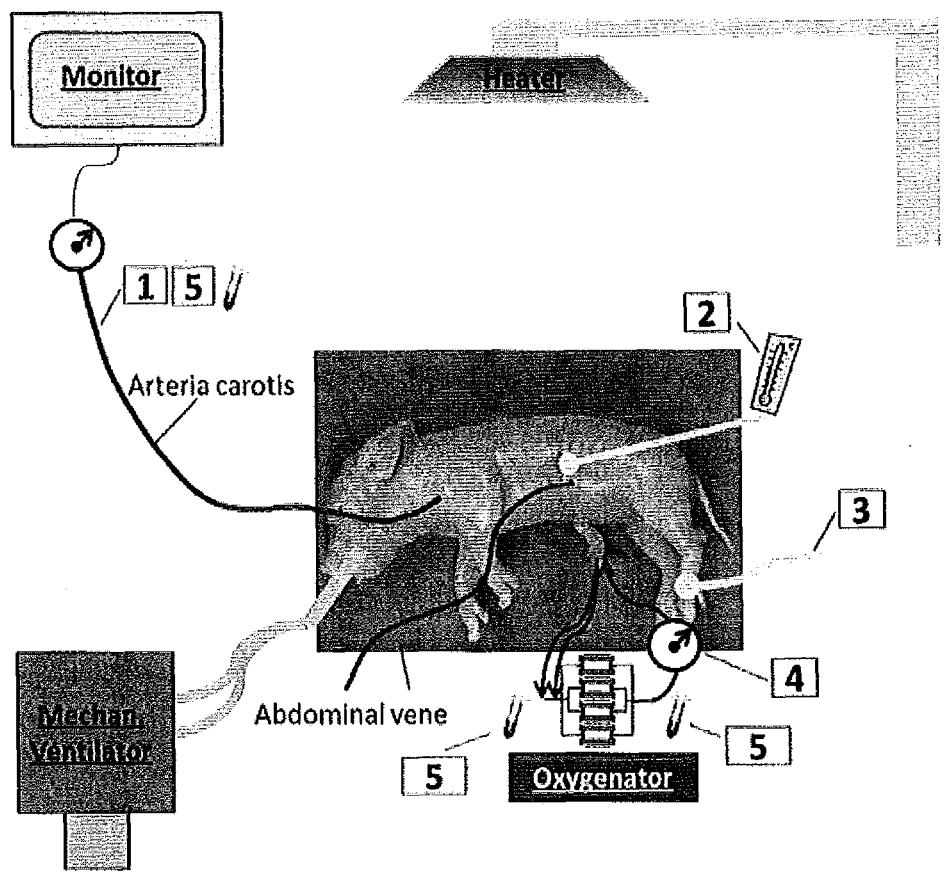
FIG. 13 is a schematic illustrating use of a placenta device in an animal model.
Figure 14:
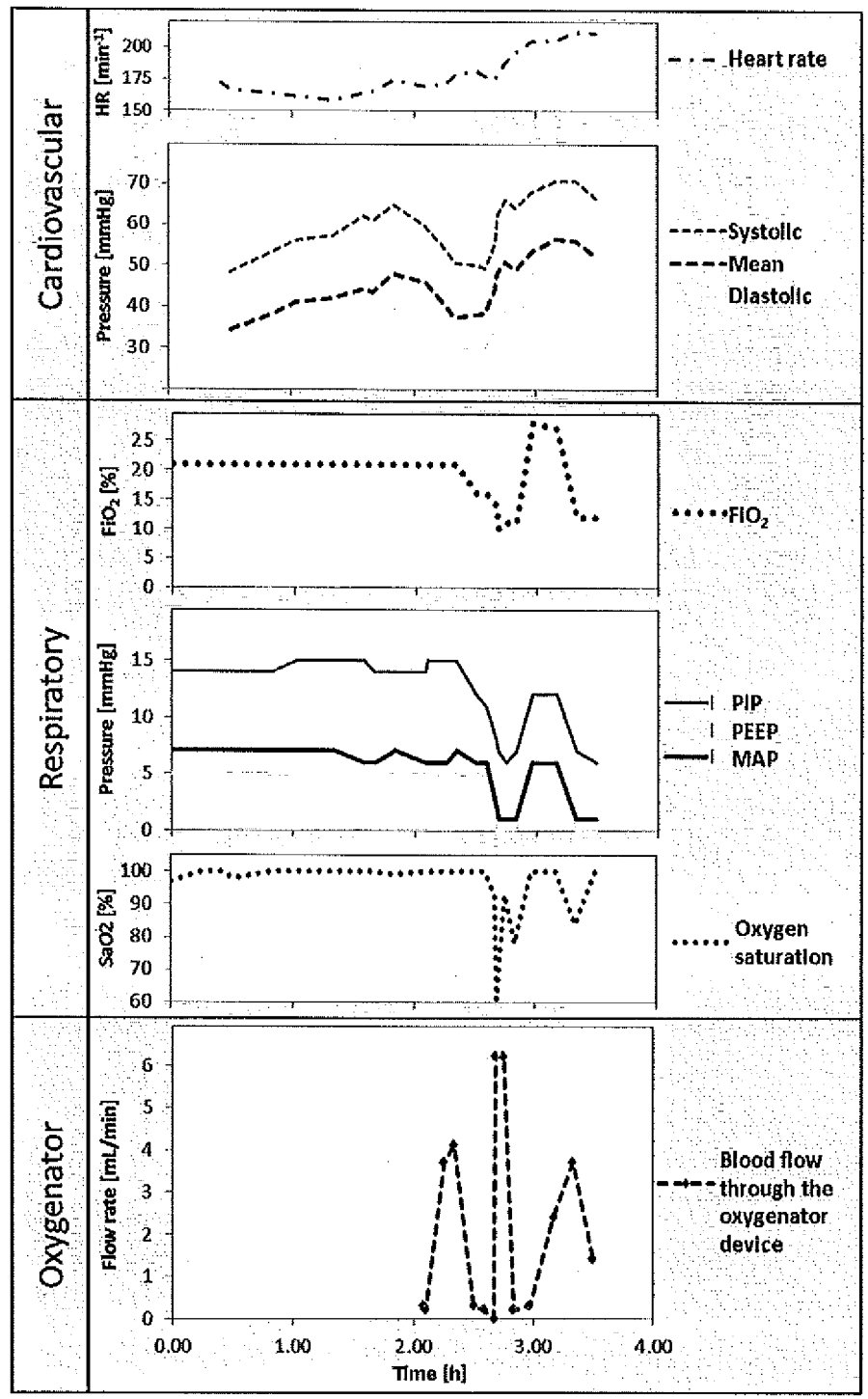
FIG. 14 shows the blood flow rate through the oxygenating placenta device, mechanical ventilator settings, and vital signs of study subject during a 3.5 hours experiment. Effectiveness of the oxygenator device was shown when blood samples taken pre- and post-oxygenator had 81% and 100% oxygen saturation respectively. Oxygen transfer was calculated to be 0.102 mL/min through the device. Figure shows heart rate ($min^{-1}$) and systolic, diastolic, and mean blood pressure (mmHg), fraction of inspired oxygen (%), peak inspiratory pressure, positive end-expiratory pressure and means airway pressure (mmHg), oxygen saturation (%) and blood flow rate through the oxygenator device (mL/min).

Throughout the experiment blood pressure, heart rate and oxygen saturation (Ohmeda Biox 3700 Pulse Oximeter, Boc Health Care, Louisville, Colo.) were monitored. Sodium phenobarbital (16 mg/kg) was given IV as required to maintain adequate sedation and regular IV pancuronium (0.2 mg/kg; Abbott Laboratories Ltd, Saint Laurent, Que.) was given to eliminate spontaneous breathing. The device was connected through the umbilical vessels. Blood was passed through the device and oxygenation was monitored throughout. FIG. 13 is a schematic illustrating the model, including monitors of blood pressure (1), body temperature (2), peripheral oxygen saturation (3), flow rate (4) and blood gases (5). Hypoxic conditions were achieved by using hypoxic gas mixtures with an adjustable O2 content of <21%.

These experiments show the feasibility of the present artificial placenta as a ventilator. The piglet was ventilated under the following settings: Fraction concentration $O_2$ (FiO$_2$)=0.12, peak inspiratory pressure=6 mbar, positive end-expiratory pressure=0 mbar and breathing frequency 35 min$^{-1}$. Throughout the experiment, cardiovascular parameters were within normal range (arterial blood pressure: 43±9 mmHg, heart rate: 180±30 min$^{-1}$ and body temperature was stable at 37.9° C. Blood flow through the device was 4 mL/min during application of device. Under hypoxic ventilator settings, the assembly composed of 14-placenta devices increased peripheral oxygen saturation by 40%.

Example 6

Evidence of Utility in Various Arrangements

Theoretical Calculations for pressure and flow characteristics of combinations of oxygenator units arranged in parallel or series were calculated as follows in Table 1.

TABLE # 1

Modeling of the resistance oxygenator units - Pressure-flow rate data for a single channel and various channels combined in various combinations of parallel and serial arrays. Numbers give units in parallel, dashes indicate serial alignment, i.e. 2-2-2-2 means 4 arrays in series consisting of two units in parallel each:

| Flow [ml/min] | Pressure 1 | In arrays 2-2-2-2 | of parallel 3-3-2 | & serial 6-2 | [mmHg] 4-4 | 8 |
|---|---|---|---|---|---|---|
| 0.5 | 18 | 43.9 | 25.2 | 14.4 | 10.6 | 2.6 |
| 0.65 | 19 | 44.8 | 25.7 | 14.7 | 10.7 | 2.6 |
| 0.8 | 20 | 45.7 | 26.1 | 14.9 | 10.8 | 2.6 |
| 0.95 | 23 | 46.7 | 26.6 | 15.2 | 10.9 | 2.6 |
| 1.1 | 26 | 47.7 | 27.0 | 15.5 | 11.0 | 2.6 |
| 1.25 | 30 | 48.7 | 27.5 | 15.8 | 11.1 | 2.6 |
| 1.4 | 33 | 49.7 | 27.9 | 16.0 | 11.2 | 2.6 |
| 1.55 | 35 | 50.8 | 28.4 | 16.3 | 11.4 | 2.7 |
| 1.7 | 37 | 51.8 | 28.9 | 16.6 | 11.5 | 2.7 |
| 1.85 | 39 | 52.9 | 29.4 | 16.9 | 11.6 | 2.7 |
| 2 | 41 | 54.1 | 29.9 | 17.2 | 11.7 | 2.7 |
| 2.15 | 43 | 55.2 | 30.4 | 17.5 | 11.8 | 2.7 |
| 2.3 | 45 | 56.4 | 31.0 | 17.9 | 12.0 | 2.7 |
| 2.4 | 46 | 57.2 | 31.3 | 18.1 | 12.1 | 2.7 |
| 2.6 | 48 | 58.8 | 32.0 | 18.5 | 12.2 | 2.8 |
| 2.9 | 52 | 61.3 | 33.2 | 19.2 | 12.5 | 2.8 |
| 3.2 | 55 | 63.9 | 34.3 | 19.9 | 12.7 | 2.8 |
| 3.5 | 58 | 66.6 | 35.5 | 20.6 | 13.0 | 2.8 |
| 3.8 | 62 | 69.5 | 36.8 | 21.4 | 13.3 | 2.9 |
| 4.1 | 64 | 72.4 | 38.0 | 22.2 | 13.6 | 2.9 |
| 4.4 | 67 | 75.5 | 39.4 | 23.0 | 13.9 | 2.9 |
| 4.7 | 71 | 78.7 | 40.8 | 23.9 | 14.2 | 3.0 |
| 4.85 | 74 | 80.4 | 41.5 | 24.3 | 14.3 | 3.0 |
| 5.15 | 81 | 83.8 | 42.9 | 25.3 | 14.6 | 3.0 |
| 5.3 | 84 | 85.6 | 43.7 | 25.7 | 14.8 | 3.0 |
| 5.45 | 89 | 87.4 | 44.5 | 26.2 | 14.9 | 3.0 |
| 5.6 | 92 | 89.2 | 45.2 | 26.7 | 15.1 | 3.1 |
| 5.75 | 96 | 91.1 | 46.0 | 27.2 | 15.2 | 3.1 |
| 5.9 | 98 | 93.1 | 46.8 | 27.7 | 15.4 | 3.1 |
| 6.05 | 107 | 95.0 | 47.7 | 28.2 | 15.6 | 3.1 |
| 6.2 | 119 | 97.0 | 48.5 | 28.8 | 15.7 | 3.1 |
| 10 |  | 164.7 | 75.7 | 46.6 | 20.5 | 3.6 |
| 15 |  | 330.2 | 137.4 | 89.4 | 29.0 | 4.3 |
| 20 |  | 662.2 | 252.8 | 174.2 | 41.1 | 5.1 |
| 25 |  | 1328.0 | 470.8 | 342.8 | 58.3 | 6.1 |
| 30 |  | 2662.9 | 886.5 | 679.4 | 82.5 | 7.2 |
| 35 |  | 5339.8 | 1685.9 | 1352.2 | 116.9 | 8.6 |
| 40 |  | 10707.4 | 3235.0 | 2698.6 | 165.5 | 10.2 |
| 45 |  | 21470.6 | 6255.3 | 5395.1 | 234.4 | 12.5 |
| 50 |  | 43053.2 | 12174.8 | 10798.0 | 332.0 | 14.5 |

The Mean arterial pressure (MAP) is 30-40 mm Hg in newborn infants. Based on calculations in Table 1 there are a number of arrangements that would minimize pressure drop across the entire device.

What is claimed is:

1. An oxygenating assembly comprising at least one pair of artificial placenta oxygenating devices for use with an infant, said artificial placenta oxygenating devices each comprising: a vascular network that permits circulation of blood therethrough, and a gas permeable membrane having first and second sides, wherein a portion of the gas permeable membrane is attached to and covers the vascular network such that the first side contacts blood within the vascular network and the second side is exposed to the atmosphere, the blood-contacting surfaces of the vascular network and gas permeable membrane are coated with an anti-coagulant, and the vascular network comprises an inlet that permits blood flow into the vascular network and an outlet that permits blood to flow out of the vascular network and wherein the inlet and outlet are positioned so that blood flows through the vascular network and in contact with the first side of the gas permeable membrane to permit gas exchange to occur, wherein each pair of placenta devices is fused back-to-back with permeable membranes exposed, and wherein the assembly comprises a main inlet which is connected via an inlet channel to the inlets of each of the placenta devices, and a main outlet which is connected via an outlet channel to the outlets of each of the placenta devices.

2. The assembly of claim 1, wherein each oxygenating device has a filling volume in the range of about 0.2 to 0.6 mL.

3. The assembly of claim 1, wherein the gas permeable membrane exhibits a permeability for oxygen of at least about 200 barrer, and a permeability for carbon dioxide of at least about 500 barrer.

4. The assembly of claim 1, wherein the vascular network exhibits a surface-to-volume ratio of blood in the range of about 100 to 130 cm-1.

5. The assembly of claim 1, wherein the ratio of the membrane connected to the vascular network versus the total membrane area is at least about 50%.

6. The assembly of claim 1, wherein the anti-coagulant is selected from the group consisting of polyethylene oxide (PEO), mixed endothelial cells, silicone, hydrophilic polymers and heparin anticoagulants.

7. The assembly of claim 1, additionally comprising a catheter attached to the main inlet and a catheter attached to the main outlet.

8. The assembly of claim 1, which is pumpless.

9. The assembly of claim 1, wherein the gas permeable membrane has a thickness of about 5-7 µm.

10. The assembly of claim 1, wherein the gas permeable membrane and vascular network are made of silicon-based polymers or polycarbonates.

11. The assembly of claim 10, wherein the silicone-based polymer is polydimethylsiloxane.

* * * * *